US008137659B2

(12) United States Patent
Kessell

(10) Patent No.: US 8,137,659 B2
(45) Date of Patent: *Mar. 20, 2012

(54) METAL OXIDE COMPOSITION

(75) Inventor: Loma Margaret Kessell, Northallerton (GB)

(73) Assignee: Croda International PLC, Goole, East Yorkshire (GB)

( * ) Notice: Subject to any disclaimer, the term of this patent is extended or adjusted under 35 U.S.C. 154(b) by 1481 days.

This patent is subject to a terminal disclaimer.

(21) Appl. No.: 10/495,490

(22) PCT Filed: Nov. 13, 2002

(86) PCT No.: PCT/GB02/05107
§ 371 (c)(1),
(2), (4) Date: Dec. 7, 2004

(87) PCT Pub. No.: WO03/041677
PCT Pub. Date: May 22, 2003

(65) Prior Publication Data
US 2008/0044483 A1    Feb. 21, 2008

(30) Foreign Application Priority Data

Nov. 14, 2001 (GB) .................. 0127325.9

(51) Int. Cl.
*A61Q 17/04* (2006.01)
*A61K 33/24* (2006.01)
*A61K 31/28* (2006.01)
*A61K 31/315* (2006.01)

(52) U.S. Cl. ........... 424/59; 424/617; 514/492; 514/494
(58) Field of Classification Search ............ 424/59, 424/617; 514/492, 494
See application file for complete search history.

(56) References Cited

U.S. PATENT DOCUMENTS

| 5,068,056 A * | 11/1991 | Robb ......................... 516/90 |
| 5,250,289 A * | 10/1993 | Boothroyd et al. ............ 424/59 |
| 5,744,126 A | 4/1998 | Horino et al. |
| 5,817,298 A | 10/1998 | Galley et al. |
| 6,217,852 B1 * | 4/2001 | Gildenberg et al. ............ 424/59 |
| 7,101,427 B2 * | 9/2006 | Dransfield et al. ............ 106/401 |
| 7,220,305 B2 * | 5/2007 | Dransfield et al. ............ 106/401 |
| 2001/0001659 A1 * | 5/2001 | Lukenbach et al. ............ 424/59 |
| 2008/0057008 A1 * | 3/2008 | Naden et al. .................... 424/59 |

FOREIGN PATENT DOCUMENTS

| DE | 3824999 | | 2/1989 |
| GB | 2217987 | | 11/1989 |
| GB | 2272691 A | * | 5/1994 |
| JP | 9100112 | | 3/1996 |
| WO | WO 90/11067 | * | 10/1990 |
| WO | WO 93/11742 | | 6/1993 |
| WO | WO 9826752 A1 | * | 6/1998 |
| WO | WO 02/00797 | | 2/2002 |

OTHER PUBLICATIONS

Convergent Cosmetics, http://home.earthlink.net/~skinesscentuals/HLBSystem.pdf, obtained Jan. 30, 2009, pp. 1-19.*
The Aldrich Catalog, 1994, p. 1442.*
Examination Report dated Jan. 26, 2007 for EP 02 781 391.4 (equivalent of U.S. Appl. No. 10/495,490).
WPI Publication No. AN 1997-276593—English Abstract of JP 9100112.
Foreign communication (First Examination Report) dated Apr. 22, 2010 for IN 1295/DELNP/2004.

* cited by examiner

Primary Examiner — Johann Richter
Assistant Examiner — Abigail Fisher
(74) Attorney, Agent, or Firm — Jones Day

(57) ABSTRACT

A composition comprises a non-ionic surfactant and hydrophobic particles of metal oxide having the mean length of the primary particles in the range from 50 to 90 nm, the mean width of the primary particles in the range from 5 to 20 nm, and the median volume particle diameter of the secondary particles is less than 45 nm. The composition is particularly suitable for use in aqueous media, and can be used in a sunscreen product that exhibits both effective UV protection and improved transparency.

26 Claims, No Drawings

METAL OXIDE COMPOSITION

CROSS REFERENCE TO RELATED APPLICATION

This application is the National Phase application of International Application No. PCT/GB02/05107, filed Nov. 13, 2002 and published in English, which designates the United States. This application, in its entirety, is incorporated herein by reference.

FIELD OF INVENTION

The present invention relates to a composition comprising hydrophobic particles of metal oxide and a non-ionic surfactant, such a composition in the form of an aqueous dispersion, and in particular to the use thereof in a sunscreen product.

BACKGROUND

Metal oxides such as titanium dioxide, zinc oxide and iron oxides have been employed as attenuators of ultraviolet light in applications such as sunscreens, plastics films and resins. Due to the increased awareness of the link between ultraviolet light and skin cancer, there has been an increasing requirement for ultraviolet light protection in everyday skincare and cosmetics products. Unfortunately, existing commercially available metal oxide products, such as titanium dioxide, are not sufficiently transparent and can have an unacceptable whitening effect when used on the skin. There is a need for a metal oxide in a form which exhibits improved transparency, reduced whitening, and provides broad spectrum ultraviolet light protection. There are particular problems involved in achieving the aforementioned properties in aqueous media.

REVIEW OF THE PRIOR ART

GB-2226018-A is directed to an aqueous dispersion of particulate acicular titanium dioxide containing an acrylic dispersing agent.

JP-07-247119 discloses an aqueous dispersion of hydrophobic titanium dioxide containing a non-ionic surfactant. The average primary particle size of the titanium dioxide is 10-100 nm.

SUMMARY OF THE INVENTION

We have now surprisingly discovered an improved metal oxide composition, which overcomes or significantly reduces at least one of the aforementioned problems.

Accordingly, the present invention provides a composition comprising at least one non-ionic surfactant and hydrophobic particles of metal oxide wherein the mean length of the primary particles is in the range from 50 to 90 nm, the mean width of the primary particles is in the range from 5 to 20 nm, and the median particle volume diameter of the secondary particles is less than 45 nm.

The present invention also provides a composition in the form of an aqueous dispersion comprising at least one non-ionic surfactant and hydrophobic particles of metal oxide wherein the mean length of the primary particles is in the range from 50 to 90 nm, the mean width of the primary particles is in the range from 5 to 20 nm, and the median particle volume diameter of the secondary particles is less than 45 nm.

The invention further provides a composition comprising at least one non-ionic surfactant and hydrophobic particles of metal oxide having an extinction coefficient at 524 nm ($E_{524}$) of less than 2.0 l/g/cm, an extinction coefficient at 450 nm ($E_{450}$) of less than 3.0 l/g/cm, an extinction coefficient at 360 nm ($E_{360}$) of greater than 3 l/g/cm, an extinction coefficient at 308 nm ($E_{308}$) of greater than 30 l/g/cm, a maximum extinction coefficient E(max) of greater than 45 l/g/cm, and a $\lambda$(max) in the range from 260 to 290 nm.

The invention still further provides a composition in the form of a sunscreen product formed from a composition comprising at least one non-ionic surfactant and hydrophobic particles of metal oxide wherein the mean length of the primary particles is in the range from 50 to 90 nm, the mean width of the primary particles is in the range from 5 to 20 nm, and the median particle volume diameter of the secondary particles is less than 45 nm.

The invention yet further provides the use of a composition comprising at least one non-ionic surfactant and hydrophobic particles of metal oxide wherein the mean length of the primary particles is in the range from 50 to 90 nm, the mean width of the primary particles is in the range from 5 to 20 nm, and the median particle volume diameter of the secondary particles is less than 45 nm, in the manufacture of a sunscreen having reduced whiteness.

Preferably the metal oxide used in the present invention comprises an oxide of titanium, zinc or iron, and most preferably the metal oxide is titanium dioxide.

The preferred titanium dioxide particles comprise anatase and/or rutile crystal form. The titanium dioxide in the particles preferably comprises a major portion of rutile, more preferably greater than 60% by weight, particularly greater than 70%, and especially greater than 80% by weight of rutile. The titanium dioxide in the particles preferably comprises in the range from 0.01 to 5%, more preferably 0.1 to 2%, and particularly 0.2 to 0.5% by weight of anatase. In addition, the titanium dioxide in the particles preferably comprises less than 40%, more preferably less than 30%, and particularly less than 25% by weight of amorphous titanium dioxide. The basic particles may be prepared by standard procedures, such as using the chloride process, or by the sulphate process, or by hydrolysis of an appropriate titanium compound such as titanium oxydichloride or an organic or inorganic titanate, or by oxidation of an oxidisable titanium compound, e.g. in the vapour state. The titanium dioxide particles are preferably prepared by the hydrolysis of a titanium compound, particularly of titanium oxydichloride.

The particles of metal oxide used in the present invention are hydrophobic. The hydrophobicity of the metal oxide can be determined by pressing a disc of metal oxide powder, and measuring the contact angle of a drop of water placed thereon, by standard techniques known in the art. The contact angle of a hydrophobic metal oxide is preferably greater than 50°.

The metal oxide particles are preferably coated in order to render them hydrophobic. Suitable coating materials are water-repellent, preferably organic, and include fatty acids, preferably fatty acids containing 10 to 20 carbon atoms, such as lauric acid, stearic acid and isostearic acid, salts of the above fatty acids such as sodium salts and aluminium salts, fatty alcohols, such as stearyl alcohol, and silicones such as polydimethylsiloxane and substituted polydimethylsiloxanes, and reactive silicones such as methylhydrosiloxane and polymers and copolymers thereof. Stearic acid and/or salt thereof is particularly preferred. The organic coating may be applied using any conventional process. Typically, metal oxide particles are dispersed in water and heated to a temperature in the range 50° C. to 80° C. A fatty acid, for example, is then deposited on the metal oxide particles by adding a salt of the fatty acid (e.g. sodium stearate) to the dispersion, followed by an acid. Alternatively, the metal oxide particles can be mixed with a solution of the water-repellent material in an organic solvent, followed by evaporation of the solvent. In an alternative embodiment of the invention, the water-repellant material can be added directly to the composition according to the present invention, during preparation thereof, such that the hydrophobic coating is formed in situ. Generally, the particles are treated with up to 25%, more preferably in the range from 3% to 20%, particularly 6% to 17%, and especially 10% to 15% by weight of organic material, preferably fatty acid, calculated with respect to the metal oxide core particles.

The particles of metal oxide may also have an inorganic coating. For example, metal oxide particles, such as titanium dioxide, may be coated with oxides of other elements such as oxides of aluminium, zirconium or silicon, or mixtures thereof such as alumina and silica as disclosed in GB-2205088-A, the teaching of which is incorporated herein by reference. The preferred amount of inorganic coating is in the range from 2% to 25%, more preferably 4% to 20%, particularly 6% to 15%, and especially 8% to 12% by weight, calculated with respect to the weight of metal oxide core particles. The inorganic coating may be applied using techniques known in the art. A typical process comprises forming an aqueous dispersion of metal oxide particles in the presence of a soluble salt of the inorganic element whose oxide will form the coating. This dispersion is usually acidic or basic, depending upon the nature of the salt chosen, and precipitation of the inorganic oxide is achieved by adjusting the pH of the dispersion by the addition of acid or alkali, as appropriate.

In a preferred embodiment of the invention, the metal oxide particles are coated with both an inorganic and an organic coating, either sequentially or as a mixture. It is preferred that the inorganic coating, preferably alumina, is applied first followed by the organic coating, preferably fatty acid and/or salt thereof. Thus, preferred metal oxide particles for use in the present invention comprise (i) in the range from 60% to 98%, more preferably 65% to 95%, particularly 70% to 80%, and especially 72% to 78% by weight of metal oxide, preferably titanium dioxide, with respect to the total weight of the particles, (ii) in the range from 0.5% to 15%, more preferably 2% to 12%, particularly 5% to 10%, and especially 6% to 9% by weight of inorganic coating, preferably alumina, with respect to the total weight of the particles, and (iii) in the range from 1% to 21%, more preferably 4% to 18%, particularly 7% to 15%, and especially 9% to 12% by weight of organic coating, preferably fatty acid and/or salt thereof, with respect to the total weight of the particles. Such metal oxide particles provide a surprising combination of both improved photostability and dispersibility.

The individual or primary metal oxide particles are preferably acicular in shape and have a long axis (maximum dimension or length) and short axis (minimum dimension or width). The third axis of the particles (or depth) is preferably approximately the same dimensions as the width. The size of the primary particles can be suitably measured using electron microscopy. The size of a particle can be determined by measuring the length and width of a filler particle selected from a photographic image obtained by using a transmission electron microscope. Mean values can be determined from the measurements of at least 300 particles, as described herein.

The mean length by number of the primary metal oxide particles is in the range from 50 to 90 nm, preferably 55 to 77 nm, more preferably 55 to 73 nm, particularly 60 to 70 nm, and especially 60 to 65 nm. The mean width by number of the particles is in the range from 5 to 20 nm, preferably 8 to 19 nm, more preferably 10 to 18 nm, particularly 12 to 17 nm, and especially 14 to 16 nm.

The size distribution of the primary metal oxide particles can also have a significant effect on the final properties of, for example, a sunscreen product comprising the metal oxide. In a preferred embodiment of the invention suitably at least 40%, preferably at least 50%, more preferably at least 60%, particularly at least 70%, and especially at least 80% by number of particles have a length within the above preferred ranges given for the mean length. In addition, suitably at least 40%, preferably at least 50%, more preferably at least 60%, particularly at least 70%, and especially at least 80% by number of particles have a width within the above preferred ranges given for the mean width.

The primary metal oxide particles suitably have a mean aspect ratio $d_1:d_2$ (where $d_1$ and $d_2$, respectively, are the length and width of the particle) in the range from 2.0 to 8.0:1, preferably 3.0 to 6.5:1, more preferably 4.0 to 6.0:1, particularly 4.5 to 5.5:1, and especially 4.5 to 5.0:1.

The primary metal oxide particles suitably have a median volume particle diameter (equivalent spherical diameter corresponding to 50% of the volume of all the particles, read on the cumulative distribution curve relating volume % to the diameter of the particles—often referred to as the "D(v,0.5)" value), measured as herein described, in the range from 20 to 35 nm, preferably 23 to 33 nm, more preferably 25 to 31 nm, particularly 25 to 28, and especially 25 to 26 nm.

In one embodiment of the invention, the primary metal oxide particles aggregate to form clusters or agglomerates of secondary particles comprising a plurality of metal oxide primary particles. The aggregation process of the primary metal oxide particles may take place during the actual synthesis of the metal oxide and/or during subsequent processing. The mean number of primary metal oxide particles present in the secondary particles according to the present invention is suitably in the range from 1 to 10, preferably 1.05 to 8, more preferably 1.1 to 5, particularly 1.3 to 3, and especially 1.4 to 2.0. Thus, statistically at least some of the secondary particles may contain only one primary particle, ie some primary particles are also secondary particles. The term "secondary" particles is partly used as a label to relate to particle size results obtained using a particular technique, as described herein.

The particulate metal oxide used in the present invention has a median volume particle diameter (equivalent spherical diameter corresponding to 50% of the volume of all the particles, read on the cumulative distribution curve relating volume % to the diameter of the particles—often referred to as the "D(v,0.5)" value)) of the secondary particles, measured as herein described, of less than 45 nm, suitably less than 40 nm, preferably less than 36 nm, more preferably in the range from 22 to 30 nm, particularly 24 to 30 nm, and especially 24 to 27 nm.

The size distribution of the secondary metal oxide particles can also be an important parameter in obtaining, for example, a sunscreen product having the required properties. The metal oxide particles suitably have no more than 16% by volume of particles having a volume diameter of less than 16 nm, preferably less than 20 nm, more preferably less than 22, particularly less than 24 nm, and especially less than 25 nm. In addition, the metal oxide particles suitably have more than 84% by volume of particles having a volume diameter of less than 50 nm, preferably less than 40 nm, more preferably less than 35, particularly less than 30 nm, and especially less than 28 nm.

It is preferred that none of the secondary metal oxide particles should have an actual particle size exceeding 150 nm. Particles exceeding such a size may be removed by milling processes which are known in the art. However, milling operations are not always totally successful in eliminating all particles greater than a chosen size. In practice, therefore, the size of 95%, preferably 99% by volume of the particles should not exceed 150 nm.

Particle size of the secondary metal oxide particles described herein may be measured by electron microscope, coulter counter, sedimentation analysis and static or dynamic light scattering. Techniques based on sedimentation analysis are preferred. The median particle size may be determined by plotting a cumulative distribution curve representing the percentage of particle volume below chosen particle sizes and measuring the 50th percentile. The median particle volume diameter of the secondary metal oxide particles is suitably measured using a Brookhaven particle sizer, as described herein.

In a particularly preferred embodiment of the invention, the metal oxide particles have a BET specific surface area, measured as described herein, of greater than 40, more preferably in the range from 50 to 100, particularly 60 to 90, and especially 65 to 75 m$^2$/g.

The metal oxide particles used in the present invention exhibit improved transparency suitably having an extinction coefficient at 524 nm ($E_{524}$), measured as herein described, of less than 2.0, more suitably less than 1.5, preferably less than 1.2, more preferably in the range from 0.1 to 1.0, particularly 0.2 to 0.9, and especially 0.3 to 0.7 l/g/cm. In addition, the metal oxide particles suitably have an extinction coefficient at 450 nm ($E_{450}$), measured as herein described, of less than 3.0, preferably in the range from 0.1 to 2.0, more preferably 0.3 to 1.7, particularly 0.5 to 1.5, and especially 0.7 to 1.0 l/g/cm.

The metal oxide particles exhibit effective UV absorption, suitably having an extinction coefficient at 360 nm ($E_{360}$), measured as herein described, of greater than 3, preferably greater than 4, more preferably in the range from 5 to 10, particularly 5.5 to 8, and especially 6 to 7.5 l/g/cm. The metal oxide particles also suitably have an extinction coefficient at 308 nm ($E_{308}$), measured as herein described, of greater than 30, preferably in the range from 35 to 65, more preferably 40 to 60, particularly 45 to 55, and especially 46 to 50 l/g/cm.

The metal oxide particles suitably have a maximum extinction coefficient E(max), measured as herein described, of greater than 45, preferably in the range from 50 to 80, more preferably 55 to 75, particularly 60 to 70, and especially 65 to 70 l/g/cm. The metal oxide particles suitably have a λ(max), measured as herein described, in the range from 260 to 290, preferably 265 to 285, more preferably 268 to 282, particularly 270 to 280, and especially 275 to 280 nm.

The metal oxide particles suitably exhibit reduced whiteness, preferably having a change in whiteness ΔL of a composition, preferably a sunscreen product, containing the particles, measured as herein described, of less than 3, more preferably in the range from 0.5 to 2.5, and particularly 1.0 to 2.0. In addition, a composition, preferably a sunscreen product, containing the particles preferably has a whiteness index, measured as herein described, of less than 100%, more preferably in the range from 10% to 80%, particularly 20% to 60%, and especially 30% to 50%.

The metal oxide particles suitably have reduced photogreying, preferably having a photogreying index, measured as herein described, of less than 15, more preferably in the range from 1 to 10, particularly 2 to 7, and especially 3 to 5.

A composition, preferably a sunscreen product, containing the metal oxide particles defined herein suitably has a Sun Protection Factor (SPF), measured as herein described, of greater than 10, preferably greater than 15, more preferably greater than 20, particularly greater than 25, and especially greater than 30 and up to 40.

In a preferred embodiment, the non-ionic surfactant used in the present invention has a HLB (Hydrophile Lipophile Balance) value of greater than 3, suitably in the range from 5 to 20, preferably 7 to 18, more preferably 9 to 16, particularly 11 to 14, and especially 12 to 13. The molecular weight (number average) of the non-ionic surfactant is suitably in the range from 150 to 2000, preferably 200 to 1500, more preferably 250 to 800, particularly 300 to 600, and especially 350 to 450.

Suitable materials include alkoxylate surfactants, and surfactants that can be derived from natural materials such as fatty acid esters, ethers, hemi-acetals or acetals of polyhydroxylic compounds or a fatty acid amide which is N-substituted with the residue of a polyhydroxylic compound.

The term alkoxylate surfactant is used to refer to compounds in which a hydrophobe, usually a hydrocarbyl group, is connected through the residue of a linking group normally having a reactive hydrogen atom to an oligomeric or polymeric chain of alkylene oxide residues. The hydrocarbyl group is typically a chain, optionally branched, preferably an alkyl chain, suitably comprising in the range from 5 to 54, preferably 6 to 36, more preferably 7 to 20, particularly 8 to 15, and especially 9 to 11 carbon atoms. The linking group can be an oxygen atom (hydroxyl group residue); a carboxyl group (fatty acid or ester residue); an amino group (amine group residue); or a carboxyamido (carboxylic amide residue). The alkylene oxide residues are typically residues of ethylene oxide ($C_2H_4O$) or propylene oxide ($C_3H_6O$) or combinations of ethylene and propylene oxide residues. When combinations are used the proportion of ethylene oxide residues are preferably at least about 50 mole %, and more preferably at least 75 mole %, the remainder being propylene oxide residues. In a particularly preferred embodiment of the invention, substantially all the residues are ethylene oxide residues. The number of alkylene oxide, preferably ethylene oxide, residues in the surfactant molecule is suitably less than 100, preferably in the range from 2 to 50, more preferably 3 to 25, particularly 4 to 15, and especially 5 to 8.

Examples of suitable alkoxylate surfactants include alcohol alkoxylates, of the formula (Ia): $R^1$—O-(AO)$_n$—H; a fatty acid alkoxylate of the formula (Ib): $R^1$—COO-(AO)$_n$—$R^2$ (plus co-products); a fatty amine alkoxylate of the formula (Ic): $R^1$—$NR^3$-(AO)$_n$—H; or a fatty amide alkoxylate of the formula (Id); $R^1$—$NR^3$-(AO)$_n$—H, where each $R^1$ is independently preferably a $C_6$ to $C_{20}$, more preferably $C_7$ to $C_{15}$, particularly $C_8$ to $C_{12}$, and especially $C_9$ to $C_{11}$, hydrocarbyl, optionally branched, preferably alkyl group; $R^2$ is a hydrogen atom or a $C_1$ to $C_6$ alkyl group; and each $R^3$ is independently a $C_1$ to $C_6$ alkyl group or a group (AO)$_n$—H; each AO is independently an ethylene oxide or propylene oxide, preferably ethylene oxide group; and the total of the indices n in the molecule is preferably in the range from 2 to 25, more preferably 3 to 15, particularly 4 to 10, and especially 5 to 7. Alkyl phenyl ethoxylates could also be used, but these are generally not now desired in personal care and cosmetic products for other reasons and are thus not usually used in the present invention. In a particularly preferred embodiment of the invention, the non-ionic surfactant comprises at least one alcohol alkoxylate as described above.

The non-ionic surfactant may be derived from natural materials, particularly vegetable, source materials. Suitable materials include a fatty acid ester, ether, hemi-acetal or acetal of a polyhydroxylic compound, or a fatty acid amide which is N-substituted with the residue of a polyhydroxylic compound, especially a saccharide fatty acid ester, and a polysaccharide stabiliser. Compositions according to the present invention may be produced which can entirely avoid using products manufactured using alkylene oxides, and thus enable the use of surfactant systems which are derived entirely from "natural" biological source, particularly vegetable source materials.

Particularly useful esters of polyhydroxylic compounds include saccharide esters particularly mono-esters of fatty acids and a sugar, especially sucrose, fructose and/or glucose. Commercially available sugar esters are usually mixtures containing mono-ester, higher esters and sometimes free starting material (sugar). In this invention it is desirable to use sugar esters having a relatively high proportion of mono-ester. Typically the sugar ester used will have a content of mono-ester of at least 50% more usually at least 60% and desirably at least 65%. Sucrose esters are particularly preferred. Such sugar esters are relatively hydrophilic surfactants and less hydrophilic variants can be used in which hydroxyl groups (usually only one) on the saccharide residue are etherified (or acetalated) typically with a $C_1$ to $C_4$ alkyl group e.g. a methyl group. Desirable sugar esters may be of the formula (IIa): $R^1$—COO—$(G)_a$, where $R^1$ is preferably as defined above for alkoxylate surfactants; each G is independently a saccharide residue, particularly a glucose, mannose or fructose residue and a is preferably from 1 to about 5, more preferably about 2, and particularly the residue $(G)_a$ is the residue of sucrose or glucose.

Other esters of polyhydroxylic compounds include esters of fatty acids, preferably fatty acids having from 8 to 24, more preferably 12 to 22, particularly 16 to 20 carbon atoms, and polyols especially glycerol, or a polyglycerol, or an anhydro-saccharide such as sorbitan. Generally, these materials are desirably also mainly used as the mono-ester. Examples include glycerol mono-laurate, triglycerol mono-stearate and among relatively more hydrophobic surfactants glycerol mono-stearate and sorbitan mono-oleate, stearate or laurate. Suitable such esters may be of the formula (IIb): $R^1$—COO—$R^4$, where $R^1$ is preferably as defined above for alkoxylate surfactants; and $R^4$ is a polyhydroxyl hydrocarbyl group, particularly an alkyl group or alkyl ether group containing from 3 to 10 carbon atoms and 2 to 6 hydroxyl groups. Such materials may be used on combination with other e.g. ester surfactants as in the blend of (nominally) polyglyceryl stearate and methyl glucoside stearate sold under the trade designation Tego Care 450 by Goldschmidt.

Other ester surfactants include fatty acid esters of hydroxycarboxylic acids, in particular the products of trans esterification between fatty glycerides, especially mono- and di-glycerides, and polyhydroxy-carboxylic acids. These products are usually described as esters, but are typically mixtures of the starting materials and the trans-esterification products, particularly where the fatty acid residues are esterified to hydroxyl groups on the hydroxycarboxylic acids. In these products, the fatty acid preferably has in the range from 8 to 24, more preferably 12 to 22, particularly 16 to 20 carbon atoms, and the hydroxycarboxylic acid is especially citric acid.

Other types of surfactants derived from sugars are saccharide hydrocarbyl ethers, hemi-acetals or acetals, commonly known as hydrocarbyl, particularly alkyl, polysaccharides (more properly oligo saccharides), and in particular materials of the formula (IIc): $R^1$—O-$(G)_a$, where $R^1$ is preferably as defined above for alkoxylate surfactants; each G is independently a saccharide residue, preferably a glucose residue and a is in the range from 1 to about 5, preferably about 1.3 to about 2.5.

A further type is of N-substituted fatty acid amides in which the N-substituent is the residue of a polyhydroxylic compound, which is commonly a saccharide residue such as a glucosyl group. This type of surfactant includes materials of the formula (IId): $R^1$—CO—$NR^5R^6$, where $R^1$ is as preferably defined above for alkoxylate surfactants; $R^5$ is a hydrogen atom, a $C_1$ to $C_6$ alkyl group or a group of the formula $R^6$; and $R^6$ is a polyhydroxyl hydrocarbyl group, preferably a group containing in the range from 3 to 10 carbon atoms and 2 to 6 hydroxyl groups, and is typically a glucosyl residue.

The concentration of non-ionic surfactant present in a composition according to the present invention is suitably in the range from 1 to 100, preferably 5 to 50, more preferably 10 to 30, particularly 13 to 25, and especially 15 to 20% by weight, calculated with respect to the weight of metal oxide particles.

In a preferred embodiment of the invention, a combination of two or more non-ionic surfactants described herein having HLB values within the above preferred ranges is employed. Suitably a mixture of two such surfactants is used which differ in molecular weights (number average), preferably by an amount in the range from 50 to 1500, more preferably 100 to 1000, particularly 250 to 700, and especially 350 to 450. The ratio by weight of the two surfactants in the composition is preferably in the range from 0.2 to 5:1, more preferably 0.5 to 2:1, particularly 0.75 to 1.3:1, and especially 0.9 to 1.1:1. Both of the surfactants are preferably alcohol alkoxylates as described above, with the total amount of surfactants present in the composition being preferably in the ranges given above for the non-ionic surfactant.

In an alternative preferred embodiment of the invention, a combination of two or more non-ionic surfactants is employed, preferably at least one relatively hydrophilic surfactant i.e. having a HLB value of greater than or equal to 9, and at least one relatively hydrophobic surfactant i.e. having a HLB value of less than 9. The hydrophilic surfactant is suitably at least one of the non-ionic surfactants described herein, preferably an alcohol alkoxylate. The hydrophilic surfactant preferably has a HLB value in the range from 9.5 to 15, more preferably 11 to 14, particularly 11.5 to 13.5, and especially 12 to 13.

The hydrophobic surfactant may also be least one of the non-ionic surfactants described herein, also suitably an alcohol alkoxylate, and preferably has a HLB value in the range from 2 to 8.5, more preferably 3 to 7.5, particularly 4 to 7, and especially 5 to 6.

When a combination of hydrophilic and hydrophobic surfactants is used, the total amount of hydrophilic and hydrophobic surfactants present in a composition according to the present invention is preferably in the ranges given above for the non-ionic surfactant. The ratio by weight of the at least one hydrophilic surfactant to the at least one hydrophobic surfactant is preferably in the range from 0.1 to 10:1, ore preferably 0.3 to 3.3:1, particularly 0.6 to 1.7, and especially 0.8 to 1.2:1.

In general, it is technically possible to freely combine non-ionic surfactants of the alkoxylate and non-alkoxylate types described above. Such combinations may be attractive where the composition includes a relatively hydrophilic alkoxylate surfactant and a relatively hydrophobic non-alkoxylate surfactant. However, hydrophilic non-alkoxylate surfactants, especially sugar mono-ester emulsifiers, are more expensive than typical alkoxylate surfactants and will usually be used only when it is desired to have a composition which includes no derivatives of alkylene oxides.

The composition comprising non-ionic surfactant and particulate metal oxide according to the present invention may be in the form of a free-flowing powder. A powder having the required particle size for the secondary metal oxide particles, as described herein, may be produced by milling processes known in the art. The final milling stage of the metal oxide is suitably carried out in dry, gas-borne conditions to reduce aggregation. A fluid energy mill can be used in which the aggregated metal oxide powder is continuously injected into highly turbulent conditions in a confined chamber where multiple, high energy collisions occur with the walls of the chamber and/or between the aggregates. The milled powder is then carried into a cyclone and/or bag filter for recovery. The fluid used in the energy mill may be any gas, cold or heated, or superheated dry steam. The non-ionic surfactant may be added at any suitable stage in the process such as prior to milling, or prior to final drying of the metal oxide.

The composition is particularly suitable for use in aqueous media, and may be formed into an aqueous slurry, or preferably an aqueous dispersion. By aqueous dispersion is meant a true dispersion, ie where the solid particles are stable to aggregation. The particles in the dispersion are relatively uniformly dispersed and resistant to settling out on standing, but if some settling out does occur, the particles can be easily redispersed by simple agitation.

A surprising feature of the present invention is that aqueous dispersions can be produced which contain at least 35, preferably at least 40, more preferably at least 45, particularly at least 50, especially at least 55, and generally up to 60% by weight of the total weight of the dispersion, of metal oxide particles. The aqueous dispersion preferably comprises in the range from 2 to 15, more preferably 4 to 12, particularly 5 to 10, and especially 6 to 8% by weight of the total weight of the dispersion, of non-ionic surfactant as defined herein.

Alternatively, the composition according to the present invention may be in the form of a lotion or cream of a solid and/or semi-solid dispersion. Suitable solid or semi-solid dispersions may contain, for example, in the range from 50 to 90, preferably 60 to 85% by weight of particulate metal oxide as defined herein, together with water, and/or a high molecular polymeric material, such as a wax.

The preferred aqueous compositions, preferably aqueous dispersions, suitably comprise at least one defoaming agent. Standard defoaming agents known in the art may be employed, preferably silicone defoaming agents. The concentration of defoaming agent present in the composition is preferably in the range from 0.1 to 5, more preferably 0.5 to 2, and particularly 0.8 to 1.2% by weight, relative to the weight of the total composition. The aqueous composition may also comprise other standard ingredients used in the art, for example preservatives.

The compositions, preferably aqueous dispersions, of the present invention are useful as ingredients for preparing sunscreen compositions, especially in the form of emulsions. The compositions may further contain conventional additives suitable for use in the intended application, such as conventional cosmetic ingredients used in sunscreens. The particulate metal oxide as defined herein, may provide the only ultraviolet light attenuators in a sunscreen product according to the invention, but other sunscreening agents, such as other metal oxides and/or other organic materials may also be added. For example, the preferred titanium dioxide particles defined herein may be used in combination with existing commercially available titanium dioxide and/or zinc oxide sunscreens. Suitable organic sunscreens for use with a composition according to the invention include p-methoxy cinnamic acid esters, salicylic acid esters, p-amino benzoic acid esters, non-sulphonated benzophenone derivatives, derivatives of dibenzoyl methane and esters of 2-cyanoacrylic acid. Specific examples of useful organic sunscreens include benzophenone-1, benzophenone-2, benzophenone-3, benzophenone-6, benzophenone-8, benzophenone-12, isopropyl dibenzoyl methane, butyl methoxy dibenzoyl methane, ethyl dihydroxypropyl PABA, glyceryl PABA, octyl dimethyl PABA, octyl methoxycinnamate, homosalate, octyl salicylate, octyl triazone, octocrylene, etocrylene, menthyl anthranilate, and 4-methylbenzylidene camphor.

In this specification the following test methods have been used:

1) Particle Size Measurement of Primary Metal Oxide Particles

A small amount of metal oxide, typically 2 mg, was pressed into approximately 2 drops of an oil, for one or two minutes using the tip of a steel spatula. The resultant suspension was diluted with solvent and a carbon-coated grid suitable for transmission electron microscopy was wetted with the suspension and dried on a hot-plate. Approximately 18 cm×21 cm photographs were produced at an appropriate, accurate magnification. Generally about 300-500 crystals were displayed at about 2 diameters spacing. A minimum number of 300 primary particles were sized using a transparent size grid consisting of a row of circles of gradually increasing diameter, representing spherical crystals. Under each circle a series of ellipsoid outlines were drawn representing spheroids of equal volume and gradually increasing eccentricity. The basic method assumes log normal distribution standard deviations in the 1.2-1.6 range (wider crystal size distributions would require many more crystals to be counted, for example of the order of 1000). The dispersion method described above has been found to be suitable for producing almost totally dispersed distributions of primary metal oxide particles whilst introducing minimal crystal fracture. Any residual aggregates (or secondary particles) are sufficiently well defined that they, and any small debris, can be ignored, and effectively only primary particles included in the count.

Mean length, mean width and length/width size distributions of the primary metal oxide particles can be calculated from the above measurements. Similarly, the median particle volume diameter of the primary particles can also be calculated.

2) Median Particle Volume Diameter Measurement of Secondary Metal Oxide Particles A dispersion of metal oxide particles was produced by mixing 104 g of deionised water, 16 g of isodecyl alcohol 6-ethoxylate, and 80 g of metal oxide. The mixture was passed through a horizontal bead mill, containing zirconia beads as grinding media, operating at approximately 1500 r.p.m. for 15 minutes. The dispersion of metal oxide particles was diluted to between 30 and 40 g/l by mixing with a 0.1% by weight aqueous solution of isodecyl alcohol 6-ethoxylate. The diluted sample was analysed on the Brookhaven BI-XDC particle sizer in centrifugation mode, and the median particle volume diameter measured.

3) BET Specific Surface Area of Metal Oxide Particles

The single point BET specific surface area was measured using a Micromeritics Flowsorb II 2300.

4) Change in Whiteness and Whiteness Index

A sunscreen formulation was coated on to the surface of a glossy black card and drawn down using a No 2 K bar to form a film of 12 μm wet thickness. The film was allowed to dry at room temperature for 10 minutes and the whiteness of the coating on the black surface ($L_F$) measured using a Minolta CR300 colourimeter. The change in whiteness $\Delta L$ was calculated by subtracting the whiteness of the substrate ($L_S$) from the whiteness of the coating ($L_F$) and expressing the value relative to the formulation containing 5% by weight of metal oxide particles. The whiteness index is the percentage change in whiteness ΔL compared to a standard titanium dioxide (=100% value) (Tayca MT100T (ex Tayca Corporation)).

5) Photogreying Index

A metal oxide dispersion was placed inside a 6 cm×3 cm acrylic cell (containing a 2 cm×1.5 cm space), and the cell made air tight by clamping a glass slide over the top, ensuring that no air bubbles were present. The initial whiteness ($L_I$) was measured using a Minolta CR300 colourimeter. The cell was then placed on a turntable revolving at 30 rpm and exposed to UV light for 2 hours (a UV lamp containing 4 TL29D, 16/09 tubes mounted 12 cm from the cell), and the whiteness ($L_T$) remeasured. The photogreying index $\Delta L = L_I - L_T$.

6) Sun Protection Factor

The Sun Protection Factor (SPF) of a sunscreen formulation was determined using the in vitro method of Diffey and Robson, J. Soc. Cosmet. Chem. Vol. 40, pp 127-133, 1989.

7) HLB Value

The HLB value of the surfactants was calculated according to the method of Schick, "Non-Ionic Surfactants", Surf. Sci. Series Vol. 1, Chapter 18.

The invention is illustrated by the following non-limiting examples.

EXAMPLES

Example 1

2 moles of titanium oxydichloride in acidic solution were reacted with 6 moles of NaOH in aqueous solution, with stirring, in a 3 litre glass vessel. After the initial reaction phase, the temperature was increased to above 70° C., by heating at a rate of approximately 1° C./min, and stirring continued for at least another 60 minutes. The mixture was then neutralised by the addition of NaOH in aqueous solution, and allowed to cool below 70° C.

To the resultant dispersion, an alkaline solution of sodium aluminate was added, equivalent to 9% by weight $Al_2O_3$ on $TiO_2$ weight. The temperature was maintained below 70° C. during the addition. The temperature was then increased to above 70° C., and stirred for at least another 10 minutes. Sodium stearate equivalent to 13.5% by weight stearate on weight of $TiO_2$ was added, and the reaction mixture again stirred for at least a further 10 minutes.

The dispersion was neutralised to pH 6.5 to 7.0 by adding 36% hydrochloric acid solution over 30 minutes. The neutralised slurry was aged for 15 minutes whilst being stirred. The slurry was then filtered to produce a filter cake which was then washed repeatedly with demineralised water until the cake conductivity (when a small sample was reslurried to 100 g/l) was less than 500 μs. The filter cake was dried in an oven at 105° C. for 16 hours and then micropulverised using a hammer mill to produce particulate titanium dioxide.

A dispersion was produced by mixing 150 g of the titanium dioxide produced above, 18 g of isodecyl alcohol 6-ethoxylate, 12 g of cetyl alcohol 10-ethoxylate, 8 g of silicone defoamer and 185 g of deionised water. The mixture was passed through a horizontal bead mill, containing zirconia beads as grinding media, operating at approximately 2100 r.p.m. for 15 minutes. A fluid dispersion was produced.

The particulate titanium dioxide and dispersion were subjected to the test procedures described herein, and exhibited the following properties:

Primary Particles
i) Mean length=63 nm,
ii) Mean width=14 nm,
iii) Mean aspect ratio=4.5,
iv) D (v,0.5)=26 nm.

Secondary Particles
i) D (v,0.5)=26 nm,
ii) 16% by volume of particles have volume diameter less than 23 nm,
iii) 84% by volume of particles have volume diameter less than 32 nm,
iv) BET specific surface area=70 m²/g, and
v) Photogreying index=3.

0.1 g of the milled titanium dioxide dispersion produced above was diluted with 100 ml of 0.1% by weight aqueous solution of isodecyl alcohol 6-ethoxylate. This diluted sample was then further diluted with the surfactant solution in the ratio sample:surfactant solution of 1:19. The total dilution was 1:20,000.

The diluted sample was then placed in a spectrophotometer (Perkin-Elmer Lambda 2 UV/VIS Spectrophotometer) with a 1 cm path length and the absorbance, of UV and visible light measured. Extinction coefficients were calculated from the equation A=E.c.l, where A=absorbance, E=extinction coefficient in litres per gram per cm, c=concentration in grams per litre, and l=path length in cm.

The results were as follows;

| $E_{524}$ | $E_{308}$ | $E_{360}$ | E(max) | λ(max) |
|---|---|---|---|---|
| 0.6 | 48 | 6.9 | 67 | 278 |

Example 2

The procedure of Example 1 was repeated except that a dispersion was produced by mixing 187 g of deionised water, 30 g of isodecyl alcohol 6-ethoxylate, 7.5 g of silicone defoamer, and 150 g of the titanium dioxide produced in Example 1. The mixture was passed through a horizontal bead mill, containing zirconia beads as grinding media, operating at approximately 2100 r.p.m. for 15 minutes. A fluid dispersion was produced.

The dispersion exhibited the following extinction coefficients;

| $E_{524}$ | $E_{308}$ | $E_{360}$ | E(max) | λ(max) |
|---|---|---|---|---|
| 0.7 | 49 | 7.0 | 69 | 278 |

Example 3

The procedure of Example 1 was repeated except that a dispersion was produced by mixing 247 g of deionised water, 24 g of isodecyl alcohol 6-ethoxylate, 24 g of oleyl alcohol 10-ethoxylate, 2.5 g of silicone defoamer, and 200 g of the titanium dioxide produced in Example 1. The mixture was passed through a horizontal bead mill, containing zirconia beads as grinding media, operating at approximately 2100 r.p.m. for 15 minutes. A fluid dispersion was produced.

The dispersion exhibited the following extinction coefficients;

| $E_{524}$ | $E_{308}$ | $E_{360}$ | E(max) | λ(max) |
|---|---|---|---|---|
| 0.7 | 50 | 7.6 | 69 | 278 |

Example 4

The titanium dioxide dispersions produced in Examples 1 and 3 were used to prepare sunscreen formulations having the following composition;

|  | % by weight |
|---|---|
| Phase A: | |
| ARLACEL 165 surfactant (ex Uniqema) | 3.0 |
| Stearyl Alcohol | 0.5 |
| SPAN 60 surfactant (ex Uniqema) | 3.0 |
| TWEEN 60 surfactant (ex Unqema) | 0.4 |
| Petroleum jelly | 3.0 |
| DC 200 fluid (ex Dow Corning) | 1.0 |
| ESTOL 3609 emollient (ex Uniqema) | 6.0 |
| PRIPURE 3759 emollient (ex Uniqema) | 8.0 |
| Antaron V-220 (ex ISP) | 2.5 |
| Phase B: | |
| Water; pure | 44.7 |
| Glycerine BP | 5.0 |
| Aloe Vera Gel 10:1 | 0.7 |
| Xanthan gum | 0.1 |
| Titanium dioxide dispersion (produced in Examples 1 or 3) | 18.8 |
| Phase C: | |
| Water; Pure | 2.5 |
| Phenonip (ex Clariant) | 0.6 |
| Germall 115 (ex ISP) | 0.3 |

The ingredients of aqueous phase B were mixed and heated to 75-80° C. The ingredients of phase A were mixed and heated to 75-80° C. and slowly added to the phase B with intensive mixing, followed by stirring with a Silverson mixer for 2 minutes. The mixture was cooled with moderate stirring and the preservative phase C added at 40-45° C.

The change in whiteness ΔL, the whiteness index and the Sun Protection Factor of the sunscreen formulations were as follows:

|  | Formulation Containing Dispersion of Example 1 | Formulation Containing Dispersion of Example 3 |
|---|---|---|
| Whiteness ΔL | 1.6 | 2 |
| Whiteness Index | 40% | 50% |
| SPF | 19 | 15 |

The above examples illustrate the improved properties of a particulate metal oxide, dispersion and sunscreen product according to the present invention.

The invention claimed is:

1. An aqueous dispersion, comprising:
   i) at least one non-ionic surfactant having an HLB value in the range from 5 to 20; and
   ii) hydrophobic particles of metal oxide having:
      a) primary particles having a mean length in the range from 50 to 90 nm and a mean width in the range from 5 to 20 nm;
      b) secondary particles, comprising clusters or agglomerates of the primary particles, having a median particle volume diameter of less than 45 nm;
      c) an extinction coefficient at 524 nm ($E_{524}$) of less than 2.0 l/g/cm; and
      d) an extinction coefficient at 308 nm ($E_{308}$) of greater than 30 l/g/cm.

2. The aqueous dispersion of claim 1, wherein the hydrophobic particles of metal oxide further comprise an extinction coefficient at 450 nm ($E_{450}$) of less than 3.0 l/g/cm, an extinction coefficient at 360 nm ($E_{360}$) of greater than 3 l/g/cm, a maximum extinction coefficient E(max) of greater than 45 l/g/cm, and a λ(max) in the range from 260 to 290 nm.

3. A sunscreen product formed from the aqueous dispersion of claim 1.

4. The aqueous dispersion of claim 1, wherein the primary particles of metal oxide have a mean length in the range from 55 to 77 nm.

5. The aqueous dispersion of claim 1, wherein the primary particles of metal oxide have a mean width in the range from 8 to 19 nm.

6. The aqueous dispersion of claim 4, wherein at least 60% by number of the primary particles have a length in the range from 55 to 77 nm and/or at least 60% by number of the primary particles have a width in the range from 8 to 19 nm.

7. The aqueous dispersion of claim 1, wherein the median particle volume diameter of the primary particles of metal oxide is in the range from 25 to 31 nm.

8. The aqueous dispersion of claim 1, wherein the median particle volume diameter of the secondary particles of metal oxide is in the range from 22 to 30 nm.

9. The aqueous dispersion of claim 1, wherein no more than 16% by volume of the secondary particles of metal oxide have a volume diameter of less than 20 nm.

10. The aqueous dispersion of claim 1, wherein more than 84% by volume of the secondary particles of metal oxide have a volume diameter of less than 40 nm.

11. The aqueous dispersion of claim 1, wherein the particles of metal oxide comprise an organic water repellant coating.

12. The aqueous dispersion of claim 1, wherein the metal oxide particles comprise (i) in the range from 65% to 95% by weight of titanium dioxide, (ii) in the range from 2% to 12% by weight of inorganic coating, and (iii) in the range from 4% to 18% by weight of organic coating, all with respect to the total weight of the particles.

13. The aqueous dispersion of claim 1, wherein the at least one non-ionic surfactant has a molecular weight in the range from 200 to 1500.

14. The aqueous dispersion of claim 1, further comprising a mixture of two non-ionic surfactants which differ in molecular weight by an amount in the range from 250 to 700.

15. The aqueous dispersion of claim 1, wherein the aqueous dispersion comprises at least 35% by weight of metal oxide particles.

16. The aqueous dispersion of claim 1, wherein the particles of metal oxide have an extinction coefficient at 524 nm ($E_{524}$) of less than 1.5 l/g/cm.

17. The aqueous dispersion of claim 2, wherein the particles of metal oxide have an extinction coefficient at 524 nm ($E_{524}$) in the range from 0.1 to 1.0 l/g/cm, an extinction coefficient at 450 nm ($E_{450}$) in the range from 0.3 to 1.7 l/g/cm, an extinction coefficient at 360 nm ($E_{360}$) in the range from 5 to 10 l/g/cm, an extinction coefficient at 308 nm ($E_{308}$) in the range from 40 to 60 l/g/cm, a maximum extinction coefficient E(max) in the range from 55 to 75 l/g/cm, and a λ(max) in the range from 260 to 290 nm.

18. The aqueous dispersion of claim 1, wherein the particles of metal oxide particles have a photogreying index in the range from 1 to 10.

19. The aqueous dispersion of claim 1, having a change in whiteness ΔL of less than 3.

20. The aqueous dispersion of claim 1, having a whiteness index in the range from 10% to 80%.

21. The aqueous dispersion of claim 1, having a Sun Protection Factor (SPF) of greater than 15.

22. The aqueous dispersion of claim 1, which is transparent when applied to the skin.

23. The aqueous dispersion of claim 1, wherein the aqueous dispersion comprises at least 40% by weight of metal oxide particles.

24. The aqueous dispersion of claim 1, wherein the at least one non-ionic surfactant has a HHB value in the range from 7 to 18.

25. The sunscreen product of claim 3, wherein the at least one non-ionic surfactant has a HLB value in the range from 7 to 18.

26. The aqueous dispersion of claim 1, wherein the concentration of the at least one non-ionic surfactant is 5 to 50% by weight, calculated with respect to the weight of the metal oxide particles.

* * * * *